(12) United States Patent
Sägmüller

(10) Patent No.: US 10,151,675 B2
(45) Date of Patent: Dec. 11, 2018

(54) METHOD AND DEVICE FOR INCREASING THE OPTICAL TRANSPARENCY OF REGIONS OF A TISSUE SAMPLE

(71) Applicant: LEICA MICROSYSTEMS CMS GMBH, Wetzlar (DE)

(72) Inventor: Bernd Sägmüller, Laudenbach (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 39 days.

(21) Appl. No.: 14/913,960

(22) PCT Filed: Aug. 26, 2014

(86) PCT No.: PCT/EP2014/068045
§ 371 (c)(1),
(2) Date: Feb. 23, 2016

(87) PCT Pub. No.: WO2015/028453
PCT Pub. Date: Mar. 5, 2015

(65) Prior Publication Data
US 2016/0231209 A1    Aug. 11, 2016

(30) Foreign Application Priority Data

Aug. 26, 2013 (DE) ........................ 10 2013 216 934

(51) Int. Cl.
| | | |
|---|---|---|
| *G01N 21/00* | (2006.01) | |
| *G01N 1/28* | (2006.01) | |
| *G01N 1/30* | (2006.01) | |
| *G01N 1/40* | (2006.01) | |
| *G01N 21/27* | (2006.01) | |
| *G01N 21/59* | (2006.01) | |
| *G01N 1/31* | (2006.01) | |
| *G01N 21/47* | (2006.01) | |
| *G01N 21/55* | (2014.01) | |

(52) U.S. Cl.
CPC ............. *G01N 1/4044* (2013.01); *G01N 1/30* (2013.01); *G01N 1/31* (2013.01); *G01N 21/272* (2013.01); *G01N 21/47* (2013.01); *G01N 21/55* (2013.01); *G01N 21/59* (2013.01); *G01N 21/5907* (2013.01); *G01N 2001/4038* (2013.01); *G01N 2201/061* (2013.01); *G01N 2201/068* (2013.01)

(58) Field of Classification Search
CPC .......... G01N 1/30; G01N 1/31; G01N 1/4044; G01N 1/28; G01N 21/00; G01N 21/272
See application file for complete search history.

(56) References Cited

U.S. PATENT DOCUMENTS

| | | | |
|---|---|---|---|
| 6,165,798 A | 12/2000 | Brooks | |
| 6,232,092 B1 | 5/2001 | Rogers | |
| 6,472,216 B1 | 10/2002 | Chiang | |
| 7,273,587 B1 | 9/2007 | Birkner et al. | |
| 8,096,982 B2 | 1/2012 | Nemati | |
| 8,554,372 B2 | 10/2013 | Windeyer et al. | |
| 2012/0196320 A1* | 8/2012 | Seibel ...................... | G01N 1/30 435/40.52 |
| 2012/0296238 A1 | 11/2012 | Chernov et al. | |
| 2013/0178916 A1 | 7/2013 | Rylander et al. | |
| 2013/0274837 A1 | 10/2013 | Nemati | |
| 2015/0144490 A1* | 5/2015 | Deisseroth ............... | G01N 1/30 204/461 |

FOREIGN PATENT DOCUMENTS

GB    2377757 A    1/2003

OTHER PUBLICATIONS

Chung et al., Structural and molecular interrogation of intact biological systems, Nature, vol. 497, pp. 332-337 Apr. 10, 2013.

\* cited by examiner

*Primary Examiner* — Ruth A Davis
(74) *Attorney, Agent, or Firm* — Hodgson Russ LLP

(57) ABSTRACT

A method for increasing the optical transparency of regions of a tissue sample (1) is proposed, in which the tissue sample (1) is introduced into a process chamber (10) and is infiltrated in the process chamber (10) with at least one process fluid (2), and in which a removal of light-scattering structures in the tissue sample (1) is carried out. The method encompasses monitoring the optical transparency of the tissue sample (1), at least during a clearing time period in which the tissue sample (1) is introduced into the process chamber (10) and in which the removal of the light-scattering structures in the tissue sample (1) is carried out, by means of an optical transparency measuring arrangement (13) associated with the process chamber (10). An apparatus (100) for carrying out the method is also a subject of the invention.

12 Claims, 2 Drawing Sheets

METHOD AND DEVICE FOR INCREASING THE OPTICAL TRANSPARENCY OF REGIONS OF A TISSUE SAMPLE

The present invention relates to a method for increasing the optical transparency of regions of a tissue sample and to an apparatus configured to carry out a corresponding method, according to the preambles of the independent claims.

BACKGROUND OF THE INVENTION

The identification of three-dimensional structural relationships in intact biological tissue specimens using micro-optical techniques conventionally entails problems due to the fact that optical transparency of such tissue samples is often largely lacking. This relates in particular to the investigation of structural relationships between neurons in nerve tissue or brain tissue. Conventional methods provide, for this purpose, for the sensing of microscopic serial sections in the form of digital images, from which a reconstruction of the three-dimensional relationships is then performed. This is, however, at least very laborious and in some cases error-prone.

In light of this, a recent publication (K. Chung et al., Structural and molecular interrogation of intact biological systems, Nature 497, 332-337, 2013) proposes a method for increasing the optical transparency of regions of a corresponding tissue sample. As explained therein, the lack of optical transparency is attributable substantially to lipid bilayers. Incoming light is scattered at interfaces formed thereby. The aforementioned publication therefore proposes the nondestructive removal of such lipid bilayers, i.e. a removal such that the remaining tissue sample is structurally maintained to the greatest possible extent.

For this the tissue sample is impregnated, for example, with hydrogel monomers (e.g. acrylamide and bisacrylamide), formaldehyde, and thermoreactive initiators. The formaldehyde on the one hand ensures crosslinking of the tissue, and on the other hand the hydrogel monomers couple covalently to biomolecules such as proteins and nucleic acids. Polymerization of the correspondingly coupled monomers is then thermally initiated to yield a hydrogel network. The aforesaid biomolecules are incorporated into the three-dimensional hydrogel thereby created, and thus stabilized.

Molecules having no couplable functional groups, in particular lipids of the lipid bilayers, remain unbound and can therefore be extracted from the structure that has been created. An ionic extraction method is usefully utilized for this, since micro-optical investigation, e.g. using fluorescence microscopy, is not thereby influenced.

For extraction of the lipids it is possible to use, for example, sodium dodecyl sulfate (SDS) micelles in aqueous solvents, which because of their net negative charge in neutral to alkaline conditions migrate in an applied electric field and can thereby be driven through the correspondingly prepared tissue sample.

Reference may be made to the aforementioned publication for further details of a corresponding method. It should be emphasized, however, that the present invention not only can be utilized in the specific method variant disclosed therein, but also can be used in other methods in which a gradual increase in the optical transparency of regions of a tissue sample can be observed at least in certain method steps.

Such methods are conventionally carried out entirely manually, i.e. the outcome of a corresponding method is monitored visually by an experimenter. Such methods are thus, in practice, work-intensive and poorly reproducible. The latter circumstance proves to be disadvantageous especially in the context of medical research projects, since its consequence is that standardized sample preparation is not possible.

The invention intends to provide a remedy here, and to simplify methods for increasing the optical transparency of regions of tissue samples and especially to improve them in terms of increased reproducibility.

DISCLOSURE OF THE INVENTION

In light of the above, the present invention proposes a method and an apparatus for increasing the optical transparency of (i.e. for "clearing") regions of a tissue sample, having the features of the independent claims. Preferred embodiments are the subject matter of the dependent claims and of the description that follows.

The present invention proceeds from a method for increasing the optical transparency of regions of a tissue sample, as previously explained in principle. In such a method, the tissue sample is introduced into a process chamber and is impregnated (infiltrated) in the process chamber with at least one process fluid. As explained, such a method can also encompass in particular the use of several process fluids that can be caused to react, for example thermally, and that crosslink structures of the tissue sample with one another and thus stabilize them.

After crosslinking or stabilization, in such a method a removal of light-scattering structures in the tissue sample is brought about, as explained earlier, for example by using surfactant micelles that migrate in an electric field. As explained, a method of this kind, conventionally carried out entirely manually, is laborious and error-prone.

When the term "process fluid" is used in the context of the present invention, this encompasses all substances (usually liquid) that can be utilized in corresponding methods in the form of individual compounds or mixtures. This refers in particular to the aforementioned process fluids that bring about optical transparency by flushing interfering structures out of the tissue sample, but also to the previously utilized stabilizing or crosslinking agents that permit subsequent unhindered flushing. Process fluids can also be storage media or embedding media. Regions of a sample whose optical transparency is increased can be, for example, membrane structures or vesicle stacks. The transparency of other regions, however, for example of the neurons to be investigated in the context of a subsequent microscopic method, remains unchanged or at least partly unchanged.

It is proposed according to the present invention to monitor the optical transparency of the tissue sample, at least during a clearing time period in which the tissue sample is introduced into the process chamber and in which the removal of the light-scattering structures in the tissue sample is brought about, by means of an optical transparency measuring arrangement associated with the process chamber.

A "clearing time period" is understood in the context of the present invention as the time period in which the actual removal of the light-scattering structures occurs. In the method explained earlier, this is the method step in which the lipid bilayers are dissolved by means of surfactant micelles and transported out of the sample. The steps already accomplished beforehand, i.e. crosslinking or stabilization of the remaining tissue constituents, do not count as part of the actual clearing time period. Monitoring can likewise occur during these preceding steps, but optionally also during subsequent steps after the clearing time period, although typically no increase in the transparency of a corresponding tissue sample is observed during such time periods.

The method according to the present invention can also encompass several clearing time periods, for example in the context of clearing using different chemical or physical methods as explained below. A monitoring operation can occur during each such clearing time period.

The present invention thus makes possible overall a standardization of a corresponding method for increasing optical transparency. Thanks to the monitoring that has been explained, which additionally can also include further monitoring methods, for example of chemical and/or physical parameters of process fluids and/or of the tissue sample, the results produced are, in particular, more reproducible as compared with the existing art. This assists the practitioner in eliminating previously existing imponderables in the context of manufacturing correspondingly transparent tissue samples.

The present invention is suitable, for example, in conjunction with micro-optical methods based on multi-photon (MP) technology or corresponding image-producing methods ("MP imaging"). Such methods are particularly suited for investigating age-related degenerative illnesses (e.g. neurodegenerative diseases) and degenerative illnesses that are attributable to the lifestyle of the patient in question (so-called "lifestyle-related" diseases). This can also be done in particular using an animal model, for example by investigating the brains of correspondingly treated mice, rats, rabbits, etc.

Thanks to the increase in optical transparency, fluorophores introduced into the tissue sample can be made more visible. Scattering by surrounding regions of the tissue sample, in particular the lipid bilayers that have been explained, is minimized or eliminated. By way of the method according to the present invention, optical penetration depths into the tissue sample of up to 5 to 6 mm, in some cases even more, for example up to 10 mm, can be achieved.

The transparency measuring arrangement used in the context of the method according to the present invention advantageously encompasses a light source and a light-sensitive detector, the tissue sample being arranged between the light source and the light-sensitive detector. A corresponding detector measures, for example, the light that proceeds from the light source, passes through the sample, and is incident onto the detector, i.e. the transmitted component thereof.

Several light sources and/or light-sensitive detectors can, however, also be used in the context of the method according to the present invention. Corresponding detectors can be used, for example, to sense scattered light that is reflected or scattered by the sample or by light-scattering structures remaining therein. A corresponding further light-sensitive detector is advantageously directed oppositely to the light emission direction of the light source or is arranged off-axis with respect to the optical axis of that light source. It can sense only a reflected, only a scattered, and/or both components of the irradiated light.

Several light sources can also be used, for example light sources that operate at different wavelengths, for example with infrared, UV, and/or (optionally colored) light in the visible wavelength region. This allows a wavelength-selective measurement of transparency, which can also be coordinated in particular with a downstream investigative method. For example, a ratio of a transmittance in the infrared to a transmittance in the ultraviolet, or respectively to a transmittance in the visible wavelength region, can be used.

In the method, at least one light property of the light furnished by the light source, and/or at least one detection property of the light-sensitive detector, can also advantageously be influenced. In both cases, for example, suitable filters can be utilized. If a selective sensing only of the unimpededly transmitted component of the light is desired, for example a first polarizing filter can be attached in front of the light source and a second, identically oriented, polarizing filter in front of the light-sensitive detector. Scattering causes the light to lose its polarization, so that in this case only the transmitted light is detected by means of the light-sensitive detector. A further detector can be embodied without a corresponding filter, so that it can sense a summed parameter of transmitted and scattered light. In this case the method according to the present invention can also encompass, for example, calculation of a difference between the transmitted and scattered light components.

The influencing of the light furnished by the light source and/or of the detection property of the light-sensitive detector can in turn be coordinated with a downstream investigative method. If a fluorescence in a specific wavelength region is to be sensed, for example, a corresponding detector can be adapted thereto and the method according to the present invention can be carried just until the detected light reaches an acceptable maximum, in order to reduce the background radiation in the downstream fluorescence method but without excessively stressing the tissue sample. A corresponding consideration applies to the light furnished by the light source.

As stated with regard to the method explained initially, methods for increasing the optical transparency of regions of tissue samples typically encompass arranging the tissue sample, during the clearing time period as explained, in a process chamber between two electrodes impinged upon at least at times by current. In this case the removal of the light-scattering structures is brought about at least in part by allowing surfactant micelles, in which, for example, the lipids of the lipid bilayers become concentrated, to migrate through the tissue sample. As explained, a method of this kind is particularly advantageous because a downstream fluorescence method is not influenced, or is very little influenced, thereby.

When a clearing operation of this kind using surfactant micelles is utilized, the method according to the present invention can in particular encompass monitoring, at least at times, a current flow between the aforesaid electrodes. For example, the progress of a corresponding clearing method can be assessed by way of changes in the current flow which correspond to changes in the migration behavior of the surfactant micelles. In addition, by way of such a current flow a defined migration speed of the micelles can be established by suitably influencing the voltage present at the electrodes. Such a method can proceed entirely automatically in the form of a control loop, so that an increase in transparency (clearing) that is particularly reproducible, and can be carried out easily by the user, can occur.

Alternatively or additionally, provision can also be made to carry out the removal of light-scattering structures at least in part by elution by means of at least one organic solvent. Such elution simplifies a corresponding method, since an electrode arrangement does not need to be used. Corresponding method steps in combination offer particular advantages; for example, portions of the light-scattering structures that cannot be eluted out of the tissue aggregate by means of the surfactant micelles can be removed by the organic solvent.

In the method explained previously, it can be particularly advantageous to monitor at least one temperature of the at least one process fluid in the process chamber. Such monitoring also contributes to an increase in the reproducibility of a corresponding method. For example, as explained above, the crosslinking of those structures of the sample which are not to be removed is, in particular, often carried out by thermally activated polymerization. Exact monitoring of a temperature profile that occurs or is used in this context allows reproducible crosslinking, and thus retention of most of the desired sample structures, to be achieved.

In all cases the present invention can also encompass the use of a vacuum infiltration or pressure infiltration operation in which the corresponding process fluids are introduced into the sample by (previous) application of a vacuum or with the aid of pressure. The method according to the present invention can encompass monitoring of a corresponding vacuum or pressure with corresponding means provided therefor. In such a case the process chamber is embodied to be vacuum- or pressure-resistant and respectively comprises an at least partly vacuum- or pressure-tight seal. Following introduction of the sample into this process chamber, the latter can be closed off, for example, by means of a correspondingly embodied cover, and further processing can be accomplished in the closed state.

It can also be advantageous at least at times to monitor at least one optical property of the at least one process fluid using the optical transparency measuring arrangement and/or a further optical arrangement. This can involve, for example, an absorption behavior at specific wavelengths. A change in absorption can come about, for example, because a reaction that is to be performed is complete and/or because the light-scattering structures have been eluted from the tissue sample. For example, in order to maintain as exactly as possible a pH value required for the respective reaction, a pH indicator, the color change of which can be monitored by means of the optical transparency measuring arrangement and/or a further optical arrangement, can also, for example, be dissolved in the at least one process fluid.

Further physical and/or chemical properties of the tissue sample and/or of the at least one process fluid can also be monitored in the context of the method according to the present invention. These are, for example, pH values, conductivity values, ionic strengths, viscosities, and the like.

A process chamber used in the context of the method according to the present invention can also comprise, in particular, means for exchanging the process fluid or fluids used. Suitable reservoir containers, for example, that are coupled by means of lines to the process chamber, can be used for this. By means of suitable pumps and/or valves that can be automatically controlled by a control unit associated with the process chamber, such process fluids can be automatically (for example, in accordance with a predefined processing protocol) mixed, temperature-controlled, and/or guided into or through the process chamber. The invention thus makes it possible overall to carry out a clearing method entirely automatically.

The method according to the present invention is particularly advantageous when the tissue sample is arranged in the process chamber with the use of position-defining means. "Position-defining means" are understood here as structures that specify or ensure a defined orientation of the sample in the process chamber. For example, a corresponding sample can be equipped with reference points or reference structures that can be aligned with corresponding reference points or reference structures in the process chamber or of a corresponding receptacle. A nonrotatable receptacle for a tissue sample is also a position-defining means.

The apparatus according to the present invention also profits from the advantages explained above. An apparatus of this kind comprises a process chamber for receiving a tissue sample in at least one process fluid for the removal of light-scattering structures in the tissue sample. According to the present invention the apparatus is notable for the fact that it comprises a transparency measuring arrangement for monitoring the optical transparency of the tissue sample at least during a clearing time period in which the tissue sample is introduced into the process chamber and in which the removal of the light-scattering structures in the tissue sample is being performed. The transparency measuring arrangement is embodied as explained.

The apparatus according to the present invention is configured in particular to carry out a method according to one of the preceding claims.

Advantageously, such an apparatus furthermore encompasses a control unit for applying control to the transparency measuring arrangement, and an evaluation unit for evaluating at least one measured signal furnished by the transparency measuring arrangement. Control application and evaluation are preferably accomplished entirely automatically, with the result that a corresponding method is carried out in particularly simple and reproducible fashion.

As likewise already explained in part, such an apparatus furthermore encompasses electrodes, impingeable upon by current, inside the process chamber, and a current source for impinging upon said electrodes. This too can respectively have control applied by the control unit and can be evaluated by the evaluation unit. The electrodes can be embodied in various ways, for example in the form of plates, grids, and/or half-cylinders, so that an optimum electric field results when they are energized.

Such an apparatus furthermore advantageously encompasses measuring means for determining at least one physical and/or chemical property of the tissue sample and/or of the at least one process fluid, and/or position-defining means for arranging the tissue sample in the process chamber. As already explained, pressure means and/or vacuum means respectively for pressure infiltration or vacuum infiltration can also be provided.

The invention and embodiments of the invention will be further explained below with reference to the attached drawings.

DETAILED DESCRIPTION OF THE DRAWINGS

Figure 1:
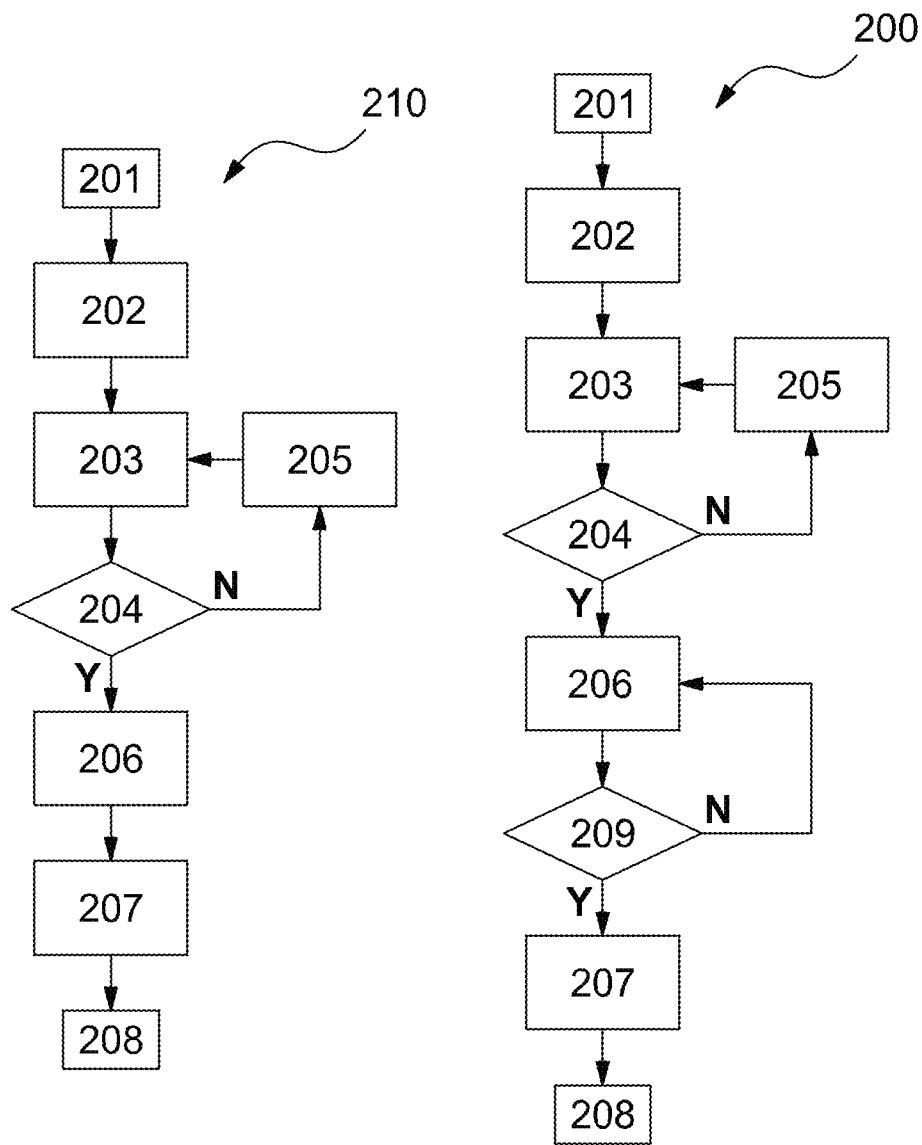
FIG. 1 illustrates in the form of a schematic flow chart a method for increasing the optical transparency of regions of a tissue sample, according to the existing art and according to an embodiment of the invention.

FIG. 1 firstly illustrates, in the form of a schematic flow chart labeled 210 in its entirety, a method according to the existing art for increasing the optical transparency of regions of a tissue sample.

It should be emphasized that corresponding methods 210 can also be carried out in a variant form, especially in consideration of the reaction principles, process media, etc.

used in each case. The number and sequence of the method steps depicted in FIG. 1 are therefore not limiting.

A corresponding method 210 is, however, always carried out before a subsequent image-producing method is carried out. Any further method steps can be provided between method 210 and subsequent image-producing method steps, for example in order to stabilize a corresponding tissue sample for storage, and the like. Further method steps that are carried before or after method 210 encompass, for example, staining, immunohistochemical labeling, or embedding of corresponding tissue samples.

Method 210 that is depicted is performed on tissue samples that have in principle been explained previously, for example on tissue samples of nerve tissue or brain tissue. Corresponding methods can also be performed on tissue samples that are present in embedded form, for example on formalin-fixed permanent specimens, forensic tissue samples, etc.

The method begins with a step 201 in which a corresponding tissue sample is furnished. In step 201, for example, a tissue sample of this kind is placed into a process chamber and secured therein.

In a subsequent step 202, addition of at least one process fluid occurs, for example in order to stabilize structures of the tissue sample as explained previously. Several corresponding steps 202 can also be carried out, successively or respectively optionally, for example in order to prepare a corresponding tissue sample for the subsequent method steps. Certain tissue samples, for example formalin-fixed permanent specimens, may require a longer sample preparation, and/or one having more steps, than other specimens, for example fresh ones.

In a step 203, for example, fixing or stabilization of the tissue sample is accomplished by crosslinking. Heating is accomplished here, for example, in order to bring about a reaction of the process fluid or fluids added in step 202. A corresponding fixing or stabilizing operation can also involve allowing further processing fluids to act, and/or establishing specific reaction conditions (temperatures, pH values, ionic strengths, etc.).

In a subsequent step 204 a check is made on the basis of known criteria as to whether step 203 was successful and/or was carried out for a long enough time. If not (No, N), then in step 205, for example, a replacement of the process fluid or fluids, a change in reaction conditions, etc. occurs. The method continues to be carried out in accordance with step 203 until success has been established in step 204 (Yes, Y).

In that case the method is continued with step 206, for example by the fact that the tissue sample is flushed and/or light-scattering structures are removed from it. In the conventional method 210, step 206 in particular is carried out and monitored entirely manually, i.e. a visual assessment is made, for example, as to whether the transparency of the sample has been sufficiently increased.

A step 207 follows, in which the tissue sample is, for example, introduced into a suitable storage fluid so that it can be stored for subsequent investigation with as little structural change as possible.

Method 210 comes to an end with step 208, in which a correspondingly prepared tissue sample exists.

A method according to an embodiment of the invention is also depicted in FIG. 1 in the form of a schematic flow chart, and is labeled 200.

Method 200 differs from method 210 explained above substantially by way of a further method step 209 that in the context of the invention encompasses monitoring, by means of an optical transparency measuring arrangement that is associated with a process chamber in which the tissue sample is present, the removal of light-scattering structures in the tissue sample. The transparency of the tissue sample increases while method step 210 is being carried out, for example during flushing of a corresponding tissue sample and/or during execution of a previously explained method using surfactant micelles. If a monitoring or check in step 209 indicates that sufficient transparency is not yet present (N), the method continues to be executed with step 206. When sufficient transparency is created (Y) the method is continued, as explained, with step 207.

Figure 2:
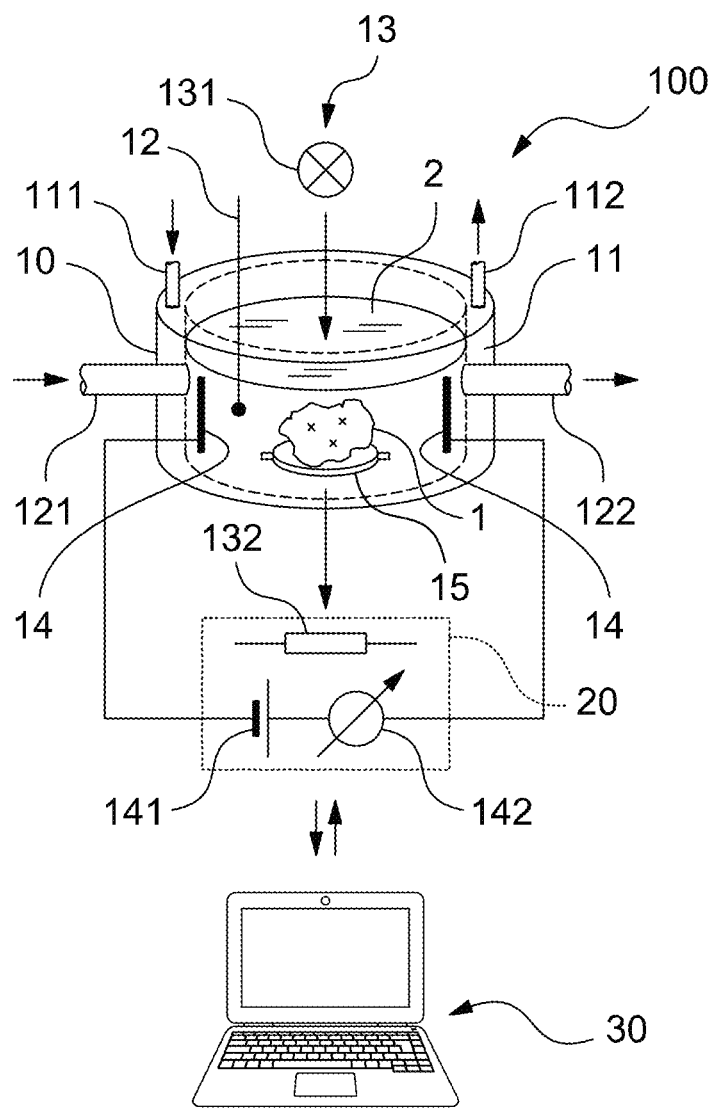
FIG. 2 schematically depicts an apparatus according to an embodiment of the invention.

FIG. 2 schematically depicts an apparatus according to an embodiment of the invention, labeled 100 in its entirety.

In the example depicted, apparatus 100 encompasses a process chamber 10 into which a process fluid 2 is introduced. A tissue sample 1 is arranged in process fluid 2 in process chamber 10. Process fluid 2 can be guided through the process chamber via suitable fluid inlets 121 and fluid outlets 122, as illustrated by the corresponding arrows in FIG. 2.

In the example depicted, the actual process chamber 10 is surrounded by a jacket region 11 that can be charged with a suitable temperature-control fluid, for example a cooling agent and/or a liquid or gaseous heating medium. This allows the temperature of process fluid 2 in process chamber 10 to be controlled. Inlets 111 and outlets 112 are provided for respectively feeding in and withdrawing such a temperature-control fluid. Alternatively to the use of a temperature-control fluid, temperature control can also be accomplished with physical means, for example by means of a resistance heating system and/or with Peltier elements.

A transparency measuring arrangement 13 that is depicted here in highly simplified fashion is associated with the process chamber. Transparency measuring arrangement 13 encompasses at least a light source 131 and a light-sensitive detector 132. In a departure from what is depicted in FIG. 2, light source 131 and light-sensitive detector 132 can also, in particular, be arranged before or after a corresponding process chamber 10, so that a corresponding tissue sample can be penetrated horizontally by the light of light source 131. As explained, several light sources 131 and/or light-sensitive detectors 132, filters, optics, and the like can be provided.

Apparatus 100 furthermore encompasses two electrodes 14. A current source 141, optionally having corresponding voltage adjusting means and/or current adjusting means 142, is provided in order to energize electrodes 14. As repeatedly explained, this allows better monitoring of an electrophoresis process that is being carried out.

Light-sensitive detector 132 and the elements just explained can be arranged in a control unit 20, illustrated here with dotted lines, that can be coupled, for example, to a computer 30. It is understood that portions of control unit 20 can also be integrated into the computer, and vice versa. Parameters of method 200 that is to be carried out can be respectively adjusted by means of control unit 20 and/or computer 30.

Apparatus 100 furthermore comprises position-defining means 15 inside process chamber 10 which are configured to arrange the tissue sample in process chamber 10, in particular to align it as previously explained.

Further sensing means 12 can also be provided inside process chamber 10 and/or externally to it, for example in order to sense a temperature, a pH value, a conductivity, an ionic strength, an oxygen saturation, a flow rate, a turbidity, a viscosity, and the like of process fluid 2 and/or of tissue sample 1, and to allow them to correspondingly affect a method that is being carried out.

The invention claimed is:

1. A method for increasing the optical transparency of regions of a tissue sample, the method comprising the steps of:
   introducing the tissue sample into a process chamber;
   infiltrating the tissue sample with at least one process fluid while the tissue sample is in the process chamber to remove light-scattering structures in the tissue sample;
   monitoring the optical transparency of the tissue sample while the tissue sample is in the process chamber, at least during a clearing time period in which the tissue sample is infiltrated with the at least one process fluid to remove light-scattering structures in the tissue sample, by automatically measuring the optical transparency of the tissue sample in the process chamber, wherein the optical transparency of the tissue sample is automatically measured by an optical transparency measuring arrangement having a light source and a light-sensitive detector, and the method further comprises the steps of positioning the tissue sample between the light source and the light-sensitive detector and controlling at least one of a polarization and a wavelength band of light provided by the light source and/or sensed by the light-sensitive detector; and
   ending the step of infiltrating the tissue sample when a sufficient optical transparency of the tissue sample is measured.

2. The method according to claim 1, wherein the step of controlling includes filtering the light emitted by the light source before such light reaches the tissue sample.

3. The method according to claim 1, wherein the step of introducing the tissue sample into a process chamber includes positioning the tissue sample in the process chamber, during the clearing time period, between electrodes, and wherein the step of infiltrating the tissue sample with at least one process fluid includes causing surfactant micelles to migrate through the tissue sample by means of the electrodes.

4. The method according to claim 3, further comprising the step of monitoring a current flow between the electrodes.

5. The method according to claim 1, in which the removal of the light-scattering structures is accomplished by elution of the tissue sample with at least one organic solvent.

6. The method according to claim 1, further comprising the step of monitoring at least one temperature of the at least one process fluid in the process chamber.

7. The method according to claim 1, further comprising the step of monitoring at least one optical property of the at least one process fluid.

8. The method according to claim 1, further comprising the step of monitoring at least one property selected from the group consisting of: a further physical property of the tissue sample other than the optical transparency, a chemical property of the tissue sample, and a chemical property of the at least one process fluid.

9. The method according to claim 1, further comprising the step of positioning the tissue sample in a defined orientation in the process chamber.

10. The method according to claim 1, wherein the step of controlling includes filtering light transmitted through the tissue sample before such light reaches the light-sensitive detector.

11. The method according to claim 1, wherein the step of controlling includes sensing only a selected wavelength band of light at the light-sensitive detector.

12. The method according to claim 1, further comprising the step of monitoring at least one optical property of the at least one process fluid using the optical transparency measuring arrangement.

* * * * *